(12) United States Patent
Roy et al.

(10) Patent No.: US 9,051,434 B2
(45) Date of Patent: *Jun. 9, 2015

(54) AMPHIPHILIC ORGANOPOLYSILOXANE DENDRIMERS WITH HIGH REFRACTIVE INDEX

(71) Applicant: Wacker Chemical Corporation, Adrian, MI (US)

(72) Inventors: Aroop K. Roy, Mechanicville, NY (US); Amitabha Mitra, Saline, MI (US); Michael L. Coffey, Adrian, MI (US)

(73) Assignee: Wacker Chemical Corporation, Adrian, MI (US)

( * ) Notice: Subject to any disclaimer, the term of this patent is extended or adjusted under 35 U.S.C. 154(b) by 200 days.

This patent is subject to a terminal disclaimer.

(21) Appl. No.: 13/755,135

(22) Filed: Jan. 31, 2013

(65) Prior Publication Data

US 2014/0212368 A1 Jul. 31, 2014

(51) Int. Cl.
| | | |
|---|---|---|
| *C07F 7/02* | (2006.01) | |
| *C07F 7/08* | (2006.01) | |
| *C08G 77/38* | (2006.01) | |
| *A61K 8/894* | (2006.01) | |
| *C08G 77/46* | (2006.01) | |
| *C08L 83/12* | (2006.01) | |
| *C08G 77/00* | (2006.01) | |

(52) U.S. Cl.
CPC ............... *C08G 77/38* (2013.01); *A61K 8/894* (2013.01); *C08G 77/46* (2013.01); *C08L 83/12* (2013.01); *C08G 77/70* (2013.01); *C08G 77/80* (2013.01)

(58) Field of Classification Search
CPC ..................................... C07F 7/04; C07F 7/08
USPC .................................................. 556/400, 465
See application file for complete search history.

(56) References Cited

U.S. PATENT DOCUMENTS

| | | |
|---|---|---|
| 5,684,112 A | 11/1997 | Berthiaume et al. |
| 5,817,302 A | 10/1998 | Berthiaume et al. |
| 6,133,370 A | 10/2000 | Gutek et al. |
| 2010/0003211 A1 | 1/2010 | Sakamoto |
| 2012/0028308 A1 | 2/2012 | Keller et al. |
| 2012/0213721 A1* | 8/2012 | Roy et al. ........................ 424/64 |

FOREIGN PATENT DOCUMENTS

WO  2012/013648 A1  2/2012

OTHER PUBLICATIONS

Walter Noll, Chemistry and Technology of Silicones, Academic Press Inc., Copyright 1968, New York, pp. 2-7.
International Search Report corresponding to PCT/EP2014/051690, dated Mar. 13, 2014.

* cited by examiner

*Primary Examiner* — Porfirio Nazario Gonzalez
*Assistant Examiner* — Kofi Adzamli
(74) *Attorney, Agent, or Firm* — Brooks Kushman P.C.

(57) ABSTRACT

Branched organopolysiloxanes of low molecular weight contain bonded arylalkyl groups. Si—C bonded surfactant groups, preferably polyoxyalkylene polyether groups, and long chain alkyl groups, exhibit a high refractive index, are completely or partially self-emulsifying, and are compatible with a variety of cosmetically acceptable oils and solvents.

13 Claims, 1 Drawing Sheet

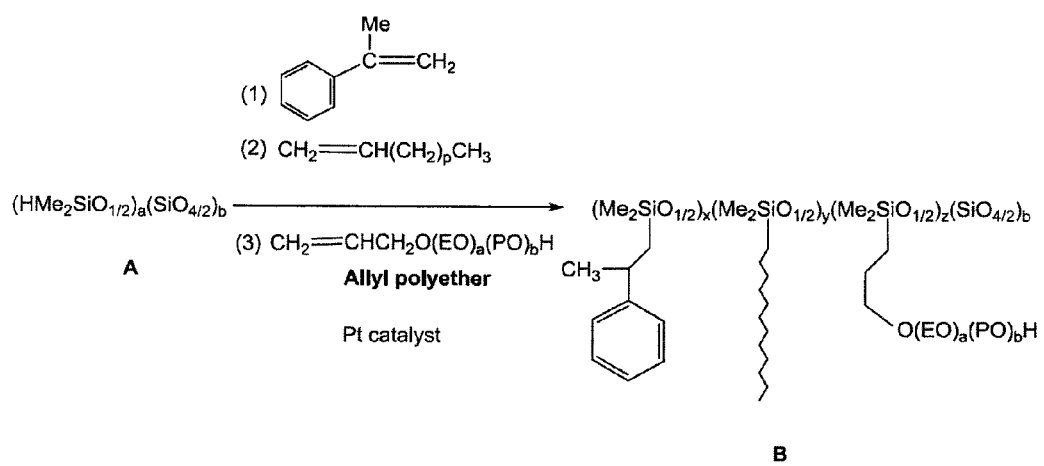

AMPHIPHILIC ORGANOPOLYSILOXANE DENDRIMERS WITH HIGH REFRACTIVE INDEX

BACKGROUND OF THE INVENTION

1. Field of the Invention

The field of the invention is directed to low molecular weight branched organopolysiloxanes which are amphiphilic and have high refractive indices, and to emulsions prepared therefrom.

2. Background Art

Organopolysiloxanes having a high refractive index have numerous uses. As neat fluids, for example, they may be used in optical devices as oils which are enclosed between optical elements. In the hair care industry, high refractive index linear organopolysiloxane fluids are useful for imparting high sheen to hair treated with formulations containing such organopolysiloxanes. These formulations are principally oil-based, since the organopolysiloxanes are usually not soluble in water. To avoid wholly oil-based products, emulsifiers may be added to emulsify the organopolysiloxane to form an oil-in-water emulsion, or the organopolysiloxane may be dissolved in another oily component and this solution is then emulsified. It is desirable to minimize the use of surfactants in such formulations.

High refractive index for silicones is mainly achieved by incorporating aryl or arylalkyl groups in the silicone structure. These arylated and arylalkylated silicones are primarily used in the oil phase of the formulation due to their compatibility with common formulation ingredients such as natural oils, synthetic esters and hydrocarbons. The trend toward water-based formulations and especially clear, water-based formulations in personal care is steadily increasing, due to the increased drive towards "natural" or "organic" compositions. There is, therefore, a perceivable demand to provide the benefit of shine/gloss via aryl-containing siloxanes that are compatible with or readily compatibilized in polar formulation media, particularly water, without significantly reducing their oil compatibility. Such amphiphilic arylalkyl containing silicones of general utility have not been available commercially.

Linear organopolysiloxanes having relatively high refractive indices are described in U.S. Pat. No. 6,133,370. The organopolysiloxanes described there contain arylalkyl groups in addition to the more common methyl substituents. To render these linear organopolysiloxanes more readily emulsifyable, polyoxyalkylene polyether substituents are also present. However, the products are not self-emulsifyable, nor do they form clear/translucent o/w microemulsions. Moreover, the increased hydrophilicity imparted by the polyether group can severely impact compatibility of the organopolysiloxane with certain oils, for example those commonly used in cosmetic applications.

U.S. published application 2012/0213721 discloses relatively high molecular weight amphiphilic linear organopolysiloxanes with a relatively high refractive index, self-emulsifiability and/or ability to form oil-in-water micro emulsion. However, this application does not disclose branched MQ type molecules, and there is no indication that a similar combination of properties will be found with a branched structure. A branched type silicone structure consisting of M and Q or T type silicone units will have different intermolecular association behavior than linear silicone units; thus, similar properties cannot be envisaged for them. However, the linear organopolysiloxanes are also self-dispersible only to a limited degree, and have only a limited range of solubility in more polar commonly used solvents such as isopropanol. A higher refractive index would also be desirable.

Organopolysiloxane MQ and MTQ resins which have high refractive indexes and hair care compositions containing them are disclosed in U.S. Pat. Nos. 5,684,112 and 5,817,302, which indicate that there is a direct correlation between silicone refractive index and gloss/shine when applied to hair. The claimed resins, however are highly condensed, thus containing numerous Q groups. The resins may optionally contain polyether groups, but there is no indication that any of the products disclosed are either self-emulsifyable in water, or are capable of forming aqueous microemulsions.

The cosmetic arts have recently described the linear silicones used in formulations such as hair care compositions as undesirably "heavy," and this may be a reflection of the high molecular weight of such linear polyorganosiloxanes.

It would be desirable to provide organopolysiloxanes of relatively low molecular weight and viscosity, i.e. not "heavy," but which have high refractive indices, which are self-dispersible or dispersible with greatly reduced levels of surfactants, thus exhibiting very good water compatibility by being capable of forming oil-in-water microemulaion or being self-emulsifiable, and which further exhibit compatibility with a wide variety of organic solvents.

SUMMARY OF THE INVENTION

It has now been surprisingly discovered that readily emulsifiable or self-dispersing organopolysiloxanes of low molecular weight, high refractive index, and high water and oil compatibility are provided by branched low molecular weight organopolysiloxanes containing M, T, and/or Q units, where the M units collectively bear arylalkyl groups, polyether groups, and long chain alkyl groups.

BRIEF DESCRIPTION OF THE DRAWINGS

FIG. 1 illustrates a reaction scheme for one embodiment of the invention.

DETAILED DESCRIPTION OF THE PREFERRED EMBODIMENT(S)

The organopolysiloxanes of the present invention may be described as low molecular weight branched MT, MQ, or MTQ organopolysiloxanes, which contain aryl moieties, polyether moieties, and long chain alkyl moieties. In the MQ organopolysiloxanes, these moieties are incorporated as substituents on the M units. In MT and MTQ organopolysiloxanes, the M units may be free of one of the aforementioned arylalkyl, polyether, or long chain alkyl groups if a corresponding group, e.g. an aryl group, arylalkyl group, alkaryl group, polyether group, or long chain alkyl group is a substituent on a T unit. However, the molecule as a whole must contain an aryl-containing group such as an aryl, arylalkyl, or alkaryl group, a polyether group, and a long chain alkyl group. The products are generally liquids, but can also be waxy solids.

The branched organopolysiloxanes of the invention thus correspond generally to the formula $$M_a T_b Q_c$$

where M, T, and Q units have their conventional meaning, for example as described by Walter Noll, CHEMISTRY AND TECHNOLOGY OF SILICONES, Academic Press, New York, pp. 2 to 7. In these organopolysiloxanes, all silicon atoms are tetravalent, preferably all silicon atoms are linked to another silicon atom or to other silicon atoms through siloxane

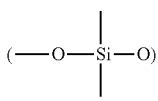

linkages, a is an integer of 3 or greater, b is 0-4, preferably 0 or 1, and c is 0-2, preferably 0 or 1, with the proviso that the sum of b and c is at least 1, and is preferably 1.

Thus, the M groups correspond to $R_e R^1_f R^2_g R^3_h SiO_{(4-(e+f+g+h))/2}$ where e, f, g, and h are all 0-3, and the sum of e, f, g, and h is 3. In these M groups, and also relevant to T groups, R is a lower alkyl group or an aryl group;
$R^1$ is an arylalkyl group;
$R^2$ is an alkylene-bonded polyether group or an alkylene-bonded polyhydroxyl compound or alkylene-bonded saccharide or derivative thereof; and
$R^3$ is a long chain alkyl group.

The T units correspond to the formula $R_e R^1_f R^2_g R^3_{h'} SiO_{(4-(e'+f'+g'+h')/2}$ where e', f', g', and h' are 0 or 1 and the sum of e', f', g', and h' is 1, where R, $R^1$, $R^2$, and $R^3$ have the same meanings as in the M units. In the $M_a T_b Q_c$ dendrimeric organopolysiloxanes, it is preferable that not more than one surfactant group be present.

The Q units correspond to the formula $SiO_{4/2}$.

R are preferably, and independently of each other, hydrocarbon groups directly bonded to silicon by Si—C bonds, which are readily available in the form of their hydrolysable silane organopolysiloxane precursors. As is well known, organopolysiloxanes are generally prepared by hydrolysis or cohydrolysis of chlorosilanes and/or alkoxysilanes. The most readily available and most inexpensive precursors contain methyl or phenyl groups as R. However, other silanes can be readily synthesized.

Thus, R may be, for example a lower alkyl group such as a methyl, ethyl, 1-propyl, 2-propyl, 1-butyl, or 2-butyl group. Hexyl and heptyl groups are also possible, but not preferred. These lower alkyl groups are also defined herein as including cyclopentyl and cyclohexyl groups, optionally methyl substituted. The aryl groups R are optionally substituted phenyl, napthyl, anthryl, and phenanthryl groups, preferred substituents being methyl and ethyl groups, when present.

$R^1$ is an arylalkyl group. These groups may initially be present in a starting hydrolysable silane, or are preferably added later by hydrosilylation, as described later; the same is true for the $R^2$ and $R^3$ groups. Preferred $R^1$ groups are arylalkyl groups where the alkyl group contains 2-6 carbon atoms, preferably 2-3 carbon atoms and most preferably 2 carbon atoms and the aryl group is an optionally substituted phenyl, napthyl, anthryl, or phenanthryl group, preferably a phenyl or naphthyl group, and most preferably a phenyl group. Among the substituents on the aryl group which are possible are preferably $C_{1-4}$ alkyl groups; halo groups such as chlorine; cyano groups; alkoxy groups, and the like. Preferably the aryl groups are unsubstituted or substituted with methyl or ethyl groups, preferably methyl groups. Cyano and chloro substitution is also preferred, as these increase the refractive index. An arylalkyl precursor is an arylalkenyl compound. Examples include styrene and α-methylstyrene, which are preferred, and m-cyanostyrene, o-cyanostyrene, and various dichlorostyrenes.

$R^2$ is an aliphatically bound surfactant group, preferably an alkylene-bonded polyoxyalkylene polyether group. As a precursor, an alkenol such as allyl alcohol can be oxyalkylated with one or more alkylene oxides in the conventional manner, for example oxyalkylation with a basic catalyst or a double metal cyanide catalyst. The alkylene oxides used include ethylene oxide, propylene oxide, and butylene oxide, although other alkylene oxides are possible, especially when used in minor proportions. Since the polyoxyalkylene polyether moiety is responsible in the largest part for the hydrophilicity and dispersibility of the inventive organopolysiloxanes, it is preferable that the polyether moieties contain predominantly oxyethylene units, i.e. greater than 50 mole percent oxyethylene units. As a second unit to be used in such polyethers, oxypropylene units are most preferred. As the amount of $C_3$ or higher oxyalkylene units increases, the hydrophilicity decreases, and dispersibility may decrease as well. Polyethers which contain a majority of oxyethylene units, for example greater than 70 mole percent, more preferably greater than 80 mole percent, yet more preferably greater than 90 mole percent, and most preferably 100% of oxyethylene units, are preferred. The non-alkenyl terminus of the polyether may be a free hydroxyl group, or it may be capped, for example, but not by limitation, with an alkyl ether or ester group.

As a result of using such precursors in the synthesis of the inventive organopolysiloxanes, $R^2$ generally is of the formula

wherein $R^5$ is a $C_{2-20}$ alkylene group, preferably an ethylene group or a propylene group, A is a $C_{2-4}$ alkylene group, which may be the same or different in the n repeating (OA) units, preferably a $C_{2-3}$ alkylene group, and most preferably an ethylene group, an n is an integer which is from 4 to 100, preferably 6-50, and more preferably 8-20. The n (OA) units, when A is different in different (OA) units, may be present in block from, random form, or combinations of these.

$R^6$ is hydrogen, alkyl, for example $C_{1-18}$ alkyl, or

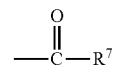

where $R^7$ is $C_{1-18}$ alkyl.

$R^2$ may also be an alkenyl-substituted polyhydroxy compound or saccharide (including polysaccharides). Polyhydroxy compounds are compounds such as polyglycerol, which contain numerous hydrophilic hydroxyl groups. Such numerous hydroxyl groups are also contained in mono- and polysaccharides such as glucose, fructose, mannose, sucrose, low molecular weight celluloses and modified celluloses, e.g. methyl cellulose, carboxymethyl cellulose, and the like. Alkenyl groups can be attached by conventional methods, such as etherification with an unsaturated alcohol such as allyl alcohol, or by esterification with an unsaturated carboxylic acid, carboxylic acid anhydride, or carboxylic acid chloride, examples being (meth)acrylic acid, (meth)acryloyl chloride, and (meth)acrylic anhydride. One process for producing unsaturated saccharides is disclosed in WO 2012/013648, while an enzymatic synthesis from unsaturated alcohol and saccharide or polysaccharide using glycosidase as a catalyst is disclosed in U.S. published application 2012/0028308 A1.

The long chain alkyl group $R^3$ is a $C_{8-40}$ alkyl group, more preferably a $C_{8-20}$ alkyl group, and most preferably a $C_{10-18}$ alkyl group. Longer chain alkyl groups confer greater oil compatibility, but may not be as readily available. The precursor to the long chain alkyl groups are the corresponding monounsaturated alkenes, preferably an α-olefin. For example, a dodecyl group precursor would be 1-dodecene. Most preferably, the long chain alkyl group contains 14 or more carbon atoms.

Most preferably, the organopolysiloxanes of the present invention are branched $Si_4$ or $Si_5$ molecules of the formulae:

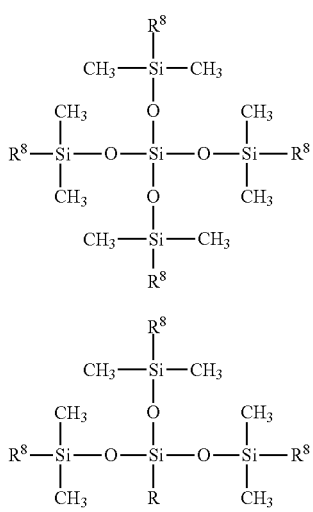

where R is preferably phenyl, and wherein each $R^8$ individually is $R^1$, $R^2$, or $R^3$, with the proviso that on average, one of each of $R^1$, $R^2$, and $R^3$ is present per molecule.

A significant advantage of the branched organopolysiloxanes of the subject invention is that they are substantially free of cyclic siloxanes, for example D4 (octamethylcyclotetrasiloxane) and D5 (decamethylcyclopentasiloxane). This is accomplished due to the method of preparation of the inventive branched organopolysiloxanes, in which the various $R^1$, $R^2$, and $R^3$ groups are preferably bonded through hydrosilylation. Also, since the linkages between $R^1$, $R^2$, and $R^3$ are by Si—C bonds, rather than Si—O—C bonds, the inventive organopolysiloxanes are stable to hydrolysis.

In the preferred method of synthesis, a branched organopolysiloxane with Si—H functionality is provided. The number of Si—H groups is preferably the same as the number of $R^1$, $R^2$, and $R^3$ groups to be attached. These starting materials are commercially available or are able to be synthesized by methods conventional in organosilicon chemistry.

For example, the Si—H functional starting materials may be formed by cohydrolysis of the respective Si—H functional silanes. For preparation of an Si—H functional starting material of formula

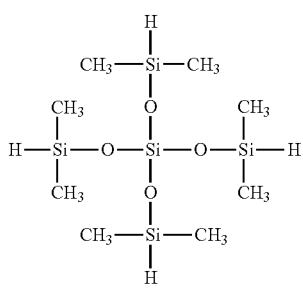

for example, four or more moles of dimethylchlorosilane may be condensed in aqueous medium, preferably aqueous alcoholic medium, with one mole of tetrachlorosilane, off-gasing HCl. Unreacted dimethylchlorosilane may be removed by distillation from a resulting non-aqueous phase containing the branched product.

The Si—H functional starting compound is then reacted with the ethylenically unsaturated $R^1$, $R^2$, and $R^3$ precursors in a noble metal catalyzed hydrosilylation reaction. The hydrosilylation catalyst may be any useful hydrosilylation catalyst. Most hydrosilylation catalysts are noble metals, or compounds or complexes of noble metals, e.g., rhodium, iridium, palladium or platinum, but platinum compounds are generally preferred due to their generally higher activity. For example, as hydrosilylation catalysts it is possible to use metals and their compounds, such as platinum, rhodium, palladium, ruthenium, and iridium, preferably platinum and rhodium. The metals may optionally be fixed to finely divided support materials, such as activated carbon, or metal oxides such as aluminum oxide or silicon dioxide. Preference is given to using platinum and platinum compounds. Particular preference is given to those platinum compounds which are soluble in polyorganosiloxanes. Soluble platinum compounds that can be used include, for example, the platinum-olefin complexes of the formulae $(PtCl_2.olefin)_2$ and $H(PtCl_3.olefin)$, preference being given in this context to the use of alkenes having 2 to 8 carbon atoms, such as ethylene, propylene, isomers of butene and of octene, or cycloalkenes having 5 to 7 carbon atoms, such as cyclopentene, cyclohexene, and cycloheptene. Other soluble platinum catalysts are the reaction products of hexachloroplatinic acid with alcohols, ethers, and aldehydes or mixtures thereof, or the reaction product of hexachloroplatinic acid with methylvinylcyclotetrasiloxane in the presence of sodium bicarbonate in ethanolic solution. Platinum catalysts with phosphorus, sulfur, and amine ligands can be used as well, e.g., $(Ph_3P)_2PtCl_2$. Particularly preferred are complexes of platinum with vinylsiloxanes, such as sym-divinyltetramethyldisiloxane. Other hydrosilylation catalysts are known from the patent and non-patent literature.

The amphiphilic silicones of the subject invention are prepared through hydrosilylation of the $R^1$, $R^2$, and $R^3$ precursors, these precursors containing a hydrosilylatable carbon-carbon multiple bond. The hydrosilylation may be concerted, pseudoconcerted, or completely stepwise relative to the addition of reactants, but is preferably stepwise. The order of hydrosilylation is not critical, but it is preferred that the arylalkene be reacted first, followed by the alkene, and finally by the alkenyl-functional hydrophilic species. It has been found that when the alkene is reacted last, that significant isomerization may occur, requiring a higher amount of alkene. Excess or unreacted $R^1$, $R^2$, or $R^3$ precursors may be removed by conventional methods, i.e. by distillation. While it is highly preferable that all unreacted $R^1$ precursors be removed, it may be advantageous for economical reasons to leave in unreacted $R^2$ precursor, which may perform the function of an emulsifier, or to leave in unreacted $R^3$ precursor, which may serve as an oily diluent.

All the synthetic routes to the inventive organopolysiloxanes preferably involve hydrosilylation, but the preceding description is not limiting. For example, instead of one or more M units containing Si—H functionality, a hydrolzable M unit containing one of $R^1$, $R^2$, or $R^3$ already bound to silicon may be used during preparation of the branched Si—H functional organopolysiloxane starting material, with the remaining $R^1$, $R^2$, or $R^3$ groups added by hydrosilylation as described above.

Thus, the preferred starting materials correspond to the formula

where i, j and k correspond, respectfully, to the values a, b, and c of the inventive organopolysiloxanes, M contains at least one silicon-bonded hydrogen atom, and preferably is of the formula $(CH_3)_2Si(H)O_{1/2}$, T is of the formula $HSiO_{3/2}$ or $BSiO_{3/2}$ where B is selected from among R, $R^1$, $R^2$, or $R^3$, and Q is $SiO_{4/2}$.

While it is possible that the substituents of the M groups of the inventive organopolysiloxanes might contain two or more $R^1$, $R^2$, or $R^3$ groups, for example by employing a starting material having M groups such as $H_3SiO_{1/2}$, or $H_2(CH_3)SiO_{1/2}$, this is not preferable. It is most preferable that the M groups individually contain but one of $R^1$, $R^2$, and $R^3$. In this case, the necessary $R^1$, $R^2$, and $R^3$ groups will be distributed among 3 or 4 or more M groups in the molecule, or among the M groups and T groups.

It is unavoidable that there will also be a proportion of organopolysiloxanes present in the product mixture which do not contain all of $R^1$, $R^2$, and $R^3$ groups. However, generally at least 30 mole percent, more preferably at least 40 mole percent, and in order of increasing preference, 50, 60, 70, and 80 mole percent or more of the molecules will contain all three of $R^1$, $R^2$, and $R^3$. It appears that a stepwise synthesis involving initial hydrosilylation of an arylalkene, followed stepwise by the long chain alkene, and finally hydrosilylation of the alkenyl-terminated polyether, results in a high proportion of product whose molecules contain all of the $R^1$, $R^2$, and $R^3$ groups. The statistical "dilution" of the desired product with organopolysiloxanes containing predominantly only two of $R^2$ and $R^3$ does not impair the usefulness of the product.

The refractive index of the amphiphilic branched organopolysiloxane is greater than 1.45, preferably greater than 1.46, and most preferably greater than 1.47. By way of comparison, a conventional polydimethylsiloxane fluid of 100 mPa·s viscosity has a refractive index of about 1.4, while a similar, phenyl substituted fluid has a refractive index of about 1.46. It was very surprising that refractive indices greater than 1.45 could be obtained while simultaneously providing for enhanced solvent compatibility, ability to form oil-in-water clear/translucent microemulsions and/or self-emulsifying properties.

Silicone-in-water (Si/W) emulsions can be readily prepared with the compositions of this invention. Particularly, Si/W micro-emulsions of the internal silicone phase particle size of 19-55 nm were achievable using common and commercially available surfactants and mixtures of surfactants. Silicone content of these emulsions can be 15-20% w/w or higher.

Even more surprisingly, compositions of this invention were self-emulsifying in water at 10% w/w or higher, depending on the respective content of $R^1$, $R^2$, and $R^3$ moieties, and the nature of the long-chain hydrocarbyl and polar polyoxyalkylene or polyhydroxy substituents, which can be determined through routine experimentation by one skilled in the art.

The branched products of the invention also can have a self-thickening property. For example, even relatively low concentration, self-emulsifying compositions can thicken to a paste upon standing. In cosmetic preparations such as creams, gels, and thick lotions, surfactants or thickeners are often added to form such products. These surfactants may at times have problems such as skin sensitivity and irritation. The products of the invention allow for the formation of creams, gels and thick lotions without requiring a thickener or surfactant, while still providing a high refractive index following application to the hair or skin.

General Synthetic Procedure

A 4-necked round-bottomed flask, equipped with various neck adapters and stopcock-equipped bypass adapter to accommodate a mechanical stirrer, thermocouple, addition funnel, water condenser, nitrogen gas inlet and outlet, and rubber septum was used for the hydrosilation. A heating mantle was used for heating the flask. An electronic thermostat was used in conjunction with the thermocouple to control heating of the flask and contents. The preparation was conducted under a mild flow of dry nitrogen gas. Upon completion of reaction, the water condenser was by-passed or removed and any volatiles were removed under vacuum. The product was cooled to below 40° C. and filtered under air or nitrogen pressure using a 0.45-10 μm nylon or polyester membrane filter with or without a pre-filter. The reactions are highly exothermic and must be controlled by adjusting the temperature and/or reagent addition rate.

EXAMPLE 1

The reaction flask was charged with tetrakis(dimethylsiloxy)silane [TDSS, 40.0 g, 1.225% w/w H content]. The flask was heated to 80° C. Alpha-methylstyrene (AMS, 28.7 g) was charged to the addition funnel, and approximately one-third of the AMS was added to the flask. The temperature of the flask contents was raised to about 100° C., and a solution of chloroplatinic acid in cyclohexanol (1% Pt w/w in the alcohol, 31 μL) was added quickly to the stirring (200-255 rpm) mixture in the flask via a syringe. A rapid exotherm ensued. AMS addition from the funnel was continued to keep the temperature in the range 140-160° C. from the heat of reaction. Upon completion of AMS addition, the mixture was heated at 145° C. for 30 minutes. The temperature was then lowered to 130° C., and 1-octene (14.2 g) was added slowly from the addition funnel.

After the octene addition had been complete, the mixture was heated for 30 minutes at 145° C. The temperature was set to 150° C., and polyoxyethylene monoallyl ether [10 mole EO, 66.7 g] addition was started at a rate of 3-4 mL/min. A further aliquot of catalyst (31 μL) was added following the start of polyether addition. The temperature was raised to 155° C. halfway through the polyether addition. The addition was completed without allowing the temperature to drop below about 150° C. At the end of the polyether addition, the temperature was raised to 155° C. The mixture was heated for one hour. Then, another aliquot of catalyst (31 μL) was added, and the mixture was heated for an additional hour. The temperature was maintained preferably in the range 155-160° C. throughout the total 2 hour mixing period since the completion of polyether addition. The reaction mixture was then stripped under vacuum (5-15 mm Hg) at about 160° C. to remove any residual volatile olefin. The off-white to straw-yellow product was then filtered after cooling to 40° C. to yield a clear, pale yellowish liquid. $^1H$ NMR analysis showed the expected product. Viscosity—98.7 mPa·s. Refractive Index—1.4742.

EXAMPLE 2

The reaction flask was charged with tetrakis(dimethylsiloxy)silane [TDSS, 41.0 g, 1.225% w/w H content]. The flask was heated to 80° C. Alpha-methylstyrene (AMS, 29.4 g) was charged to the addition funnel, and approximately one-third of the AMS was added to the flask. The temperature of the flask contents was raised to about 100° C., and a solution of chloroplatinic acid in cyclohexanol (1% Pt w/w in the alcohol, 31 μL) was added quickly to the stirring (200-255 rpm) mixture in the flask via a syringe. A rapid exotherm ensued. AMS addition from the funnel was continued to keep the temperature in the range 140-160° C. from the heat of reaction. Upon completion of AMS addition, the mixture was heated at 145° C. for 30 minutes. The temperature was then lowered to 140° C., and 1-octadecene (33.0 g) was added slowly from the addition funnel. Immediately after the start of octadecene addition, an aliquot of Pt catalyst (15 μL) was added. After the octadecene addition had been complete, the mixture was heated for 30 minutes at 145° C. The temperature was set to 150° C., and polyoxyethylene monoallyl ether [10 mole EO, 63.0 g] addition was started at a rate of 3-4 mL/min. A further aliquot of catalyst (31 μL) was added following the start of polyether addition. The temperature was raised to 155° C. halfway through the polyether addition. The addition was completed without allowing the temperature to drop below about 150° C. At the end of the polyether addition, the temperature was raised to 155 C. The mixture was heated for one hour. Then, another aliquot of catalyst (31 μL) was added, and the mixture was heated for an additional hour. The temperature was maintained preferably in the range 155-160° C. throughout the total 2 hour mixing period since the completion of polyether addition. The reaction mixture was then stripped under vacuum (5-15 mm Hg) at about 160-180° C. to remove any residual volatile olefin. The off-white to straw-yellow product was then filtered after cooling to 40° C. to yield a clear, pale yellowish liquid. 1H NMR analysis showed the expected product. Viscosity—157 mPa·s. Refractive Index—1.4730.

EXAMPLE 3

Using a procedure very similar to that of Example 2, tetrakis(dimethylsiloxy)silane [TDSS, 36.0 g, 1.225% w/w H content] was allowed to react with AMS (25.4 g), 1-octadecene (28.5 g) and polyoxyethyleneoxypropylene monoallylether (20 mole EO-20 mole PO, 216.4 g), in that order of olefin addition. The first aliquot of catalyst was added at ~100° C. The start temperature for octadecene addition was 140° C., and the temperature during the addition was kept below 155° C. by controlling the addition rate. The Pt catalyst used was chloroplatinic acid in cyclohexanol (1.0% w/w Pt, total catalyst volume 108 μL). The crude product was stripped under vacuum at 22 mm Hg and 160° C. and filtered to yield an almost clear, colorless liquid. NMR analysis showed the expected product. Viscosity—391 mPa·s. Refractive Index—1.4625.

EXAMPLE 4

Using a procedure very similar to that of Example 2, phenyltris(dimethylsiloxy)silane [Ph TDSS, 25.0 g, 0.897% w/w H content] was allowed to react with AMS (8.73 g), 1-octadecene (19.7 g) and polyoxyethylene monoallyl ether [10 mole EO, 40.6 g], in that order of olefin addition. The first aliquot of catalyst was added at ~100° C. The start temperature for octadecene addition was 140° C., and the temperature during the addition was kept below 155° C. by controlling the addition rate. The Pt catalyst used was chloroplatinic acid in cyclohexanol (1.0% w/w Pt, total catalyst volume 42 μL). The crude product was stripped under vacuum at 14 mm Hg and ~160° C. and filtered to yield an almost clear, colorless liquid. NMR analysis showed the expected product. Viscosity—144 mPa·s. Refractive Index—1.4764.

EXAMPLE C5 (COMPARATIVE EXAMPLE)

Using a procedure very similar to that of Example 2, tetrakis(dimethylsiloxy)silane [TDSS, 56.0 g, 1.205% w/w H content] was allowed to react with AMS (39.5 g) and 1-octene (41.2 g), in that order of olefin addition. The first aliquot of catalyst was added at ~100° C. The start temperature for octene addition was 110° C., and the temperature during the addition was kept below 140° C. by controlling the addition rate. After the octene addition had been complete, the mixture was heated for 60 minutes at 135° C. The Pt catalyst used was chloroplatinic acid in cyclohexanol (1.0% w/w Pt, total catalyst volume 43 μL, 3 ppm Pt). The crude product was stripped under vacuum at 31 mm Hg and 150° C. and filtered to yield a clear, pale yellow liquid. NMR analysis showed the expected product. Viscosity—18 mPa·s. Refractive Index—1.471.

EXAMPLE C6 (COMPARATIVE EXAMPLE)

Using a procedure very similar to that of Example 2, tetrakis(dimethylsiloxy)silane [TDSS, 68.0 g, 1.225% w/w H content] was allowed to react with AMS (24.3 g) and 1-dodecene (109 g), in that order of olefin addition. The first aliquot of catalyst was added at ~100° C. The start temperature for dodecene addition was ~140° C., and the temperature during the addition was kept below 155° C. by controlling the addition rate. After the dodecene addition had been complete, the mixture was heated for 3.5 hours at 145-150° C. The Pt catalyst used was chloroplatinic acid in cyclohexanol (1.0% w/w Pt, total catalyst volume 130 μL, 3 ppm Pt). The crude product was stripped under vacuum at 16 mm Hg and 160° C. and filtered to yield a clear, pale yellow liquid. NMR analysis showed the expected product. Viscosity—27 mPa·s. Refractive Index—1.457.

EXAMPLE 7

Using the product of Example 3, a silicone-in-water (Si/W) micro-emulsion was prepared. Thus, into a beaker containing de-ionized water (14.6 g), were added with constant shearing the surfactants Genapol X 100 (17.6 g), Lutensol TO5 (2.0 g), Lutensol AT25 (2.0 g) in that order, followed by the silicone fluid (30 g), glycerin (2.0 g) and water (131.8 g). The wall of the beaker was scraped as needed to ensure complete incorporation of the grease phase into the emulsion, and the temperature of the mixture was not allowed to rise above about 60° C. The emulsion was filtered after cooling as needed. This yielded a transparent micro-emulsion of the silicone fluid. Mean particle size of internal phase: 19.5 nm.

EXAMPLE 8

In a manner similar to Example 7, the silicone fluid of Comparative Example C5 yielded a milky white macro-emulsion using the composition: water (14.6 g), Genapol X 100 (17.6 g), Lutensol TO5 (2.0 g), Lutensol AT25 (2.0 g), silicone fluid (30 g), glycerin (2.0 g) and water (131.8 g). Mean particle size of internal phase: 190.0 nm.

EXAMPLE 9

The silicone fluid of Example 1 readily self-emulsified at 10% w/w in deionized water to a translucent emulsion.

EXAMPLE 10

The silicone fluid of Example 2 readily self-emulsified at 10% w/w level in deionized water to form an emulsion. The emulsion self-thickened to a white paste on standing.

EXAMPLE 11

The silicone fluid of comparative Example C5 did not self-emulsify at 10% w/w in deionized water.

Solubility of compositions of present invention at 10% w/w at room temperature in various common personal care solvents (S=soluble, I=insoluble, SC=slightly cloudy):

|  | Example 1 | Example 2 | Example 3 | Example 4 |
|---|---|---|---|---|
| Ethyl alcohol | S | S | S | S |
| Isopropyl alcohol | S | S | S | S |
| Isopropyl palmitate | S | S | S | SC |
| Dicaprylyl carbonate | S | S | S | S |
| C12-15 alkyl benzoate | S | S | S | S |
| Isoodecane | I | S | I | I |
| Castor Oil | S | S | S | S |

The experimental examples above show that a combination of high refractive index, amphiphilicity and self-emulsification properties and/or ability to form microemulsions can be found only with a combination of aralkyl, alkyl and polyether groups in the same molecule in the manner described. A comparative example that has a branched structure but a combination of only aralkyl and alkyl groups, although having a high refractive index, does not form an o/w microemulsion; rather it just forms a milky white macroemulsion.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A liquid or solid branched organopolysiloxane of the formula $$M_a T_b Q_c$$

where a is at least 3, b is 0-4, and c is 0-2;
where M is a monovalent siloxy unit of the formula $$R_e R^1_f R^2_g R^3_h SiO_{(4-(e+f+g+h))/2}$$

where e, f, g, and h are individually integers from 0 to 3 and the sum (e+f+g+h) equals 3;
R is a lower alkyl group or an aryl group,
R$^1$ is an arylalkyl group
R$^2$ comprises an alkylene-bonded surfactant group selected from the group consisting of polyoxyalkylene polyethers, polyhydroxyl compounds, and saccharides,
R$^3$ is a long chain alkyl group having 8-40 C atoms;
where T is a trivalent siloxy unit of the formula $$R_{e'} R^1_{f'} R^2_{g'} R^3_{h'} SiO_{(4-(e'+f'+g'+h'))/2}$$

where the sum (e'+f'+g'+h') is 1;
where Q units are of the formula SiO$_{4/2}$,
with the proviso that the refractive index of the organopolysiloxane or dendrimer is ≥1.45, and the organopolysiloxane or dendrimer is self-emulsifyable in water at 10% by weight relative to the total weight of water and organopolysiloxane or dendrimer, and the organopolysiloxane or dendrimer contains at least one of each of R$^1$, R$^2$, and R$^3$.

2. The branched organopolysiloxane of claim 1, wherein the long chain alkyl group is a C$_{8-20}$ alkyl group.

3. The branched organopolysiloxane of claim 1, wherein the long chain alkyl group contains 14 or more carbon atoms.

4. The branched organopolysiloxane of claim 1, wherein the alkylene-bonded polyoxyalkylene polyether group is present and is of the formula $$—R^5—(OA)_n—OR^6$$

where R$^5$ is C$_{2-20}$ alkylene group, A may be the same or different and is a C$_{2-4}$ alkylene group, n is an integer from 4 to 100, and R$^6$ is hydrogen, alkyl, or

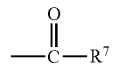

where R$^7$ is C$_{1-18}$ alkyl.

5. The branched organopolysiloxane of claim 4, wherein (OA) units comprise oxyethylene and optionally oxypropylene units, and when both oxyethylene and oxypropylene units are present, they may be present in any order.

6. The branched organopolysiloxane of claim 5, wherein the oxyethylene units are present in block form.

7. The branched organopolysiloxane of claim 1, having the formula M$_a$T$_b$.

8. The branched organopolysiloxane of claim 1, which is a dendrimer of the formula M$_3$T.

9. The branched organopolysiloxane of claim 1, which is a dendrimer of the formula M$_4$Q.

10. The branched organopolysiloxane of claim 1 which is self-dispersible in water.

11. The branched organopolysiloxane composition of claim 1, which is in the form of an aqueous dispersion.

12. The branched organopolysiloxane composition of claim 1, which is in the form of a silicone-in-water microemulsion.

13. The branched organopolysiloxane composition of claim 1, which is self-thickening in water.

* * * * *

UNITED STATES PATENT AND TRADEMARK OFFICE
CERTIFICATE OF CORRECTION

| | | |
|---|---|---|
| PATENT NO. | : 9,051,434 B2 | Page 1 of 1 |
| APPLICATION NO. | : 13/755135 | |
| DATED | : June 9, 2015 | |
| INVENTOR(S) | : Aroop K. Roy et al. | |

It is certified that error appears in the above-identified patent and that said Letters Patent is hereby corrected as shown below:

In the Claims

Column 12, Line 4, Claim 1

After "alkyl group having"

Delete "840C atoms" and

Insert -- 8-40C atoms --.

Signed and Sealed this
Twenty-third Day of February, 2016

Michelle K. Lee
*Director of the United States Patent and Trademark Office*